US008524447B2

(12) United States Patent
Noji et al.

(10) Patent No.: US 8,524,447 B2
(45) Date of Patent: Sep. 3, 2013

(54) FLUORESCENTLY LABELED FUSION PROTEIN FOR ASSAYING ADENOSINE TRIPHOSPHATE

(75) Inventors: Hiroyuki Noji, Suita (JP); Hiromi Imamura, Suita (JP); Ryota Iino, Suita (JP); Yasuyuki Yamada, Tokyo (JP)

(73) Assignee: The New Industry Research Organization, Hyoko (JP)

( * ) Notice: Subject to any disclaimer, the term of this patent is extended or adjusted under 35 U.S.C. 154(b) by 765 days.

(21) Appl. No.: 12/594,198

(22) PCT Filed: Mar. 25, 2008

(86) PCT No.: PCT/JP2008/055535
§ 371 (c)(1),
(2), (4) Date: Jan. 5, 2010

(87) PCT Pub. No.: WO2008/117792
PCT Pub. Date: Oct. 2, 2008

(65) Prior Publication Data
US 2010/0233692 A1 Sep. 16, 2010

(30) Foreign Application Priority Data
Mar. 27, 2007 (JP) ................. 2007-082560

(51) Int. Cl.
  C12Q 1/68    (2006.01)
  C12Q 1/02    (2006.01)
  C12N 9/00    (2006.01)
  C12N 15/63   (2006.01)

(52) U.S. Cl.
  USPC .............. 435/6; 435/183; 435/29; 435/320.1; 536/23.2

(58) Field of Classification Search
  None
  See application file for complete search history.

(56) References Cited

FOREIGN PATENT DOCUMENTS
EP    1 041 151 A1    10/2000
JP    2007151498   *  6/2007

OTHER PUBLICATIONS

Iino R, Murakami T, Iizuka S, Kato-Yamada Y, Suzuki T, Yoshida M.Real-time monitoring of conformational dynamics of the epsilon subunit in F1-ATPase.J Biol Chem. Dec. 2, 2005;280(48):40130-4. Epub Oct. 3, 2005.*
Hideto Takami, Yoshihiro Takaki, Gab-Joo Chee, Shinro Nishi, Shigeru Shimamura, Hiroko Suzuki, Satomi Matsui, and Ikuo Uchiyama. Thermoadaptation trait revealed by the genome sequence of thermophilic Geobacillus kaustophilus Nucl. Acids Res. 2004; 32(21): 6292-6303.*
Santana M, Ionescu MS, Vertes A, Longin R, Kunst F, Danchin A, Glaser P.Bacillus subtilis F0F1 ATPase: DNA sequence of the atp operon and characterization of atp mutants.J Bacteriol. Nov. 1994;176(22):6802-11.*
M Willemse, E Janssen, F de Lange et al. ATP and FRET—a cautionary note. Nature Biotechnology 25, 170-172 (2007) doi:10.1038/nbt0207-170.*

Yag; et al., "Structures of the thermophilic F1-ATPase E subunit suggesting ATP-regulated arm motion of its C-terminal domain in F1," PNAS 104(27):11233-11238, Jul. 3, 2007.
Imamura et al., "Visualization of ATP levels inside single living cells with fluorescence resonance energy transfer-based genetically encoded indicators," PNAS 105(37),15651-15656, Sep. 15, 2009.
Kato et al. "Roie of the E subunit of Thermophilic F1-ATPase as a Sensor for ATP," J. of Biological Chemistry, 282(52):37618-37623, Dec. 28, 2007.
Uhlin et al., "Crystal structure of the E subunit of the protein-translocating ATP synthase from E. coli," Structure 5:1219-1230, Sep. 15, 1997.
Kato-Yamada ,Y and Yoshida M., Isolated epsilon subunit of thermophilic F1-ATPase binds ATP., J. Biol. Chem., 2003, vol. 278, No. 38, p. 36013-36016.
Iino, R., et al., "Keiko Kyomei Energy Ido o Mochiita FOF1-ATP Gosei Koso Epsilon Subunit no Kozo Henka no Kenshutsu," Biophysics, The Biophysical Society of Japan Dai: 40 Kai Nenkai Koen Yokoshu, 2002, vol. 42, Sup. 2, p. S147 (201615).
Yasuda, R., et al., "The ATP-waiting conformation of rotating F1-ATPase revealed by single-pair fluorescence resonance energy transfer.," Proc Natl Acad Sci USA, 2003, vol. 100, No. 16, p. 9314-9318.
Kato-Yamada, Y., et al., "Movement of the helical domain of the epsilon subunit is required for the activiation of thermophilic F1-ATPase.," J. Biol. Chem., 2000, vol. 275, No. 46, p. 35746-35750.
Kato-Yamada, Y., "Isolated epsilon subunit of Bacillus subtilis F1-ATPase binds ATP.," FEBS Lett., 2005, vol. 579, No. 30, p. 6875-6868.
Iino, R., et al., "Real-time monitoring of conformational dynamics of the epsilon subunit in F1-ATPase.," J. Biol. Chem., 2005, vol. 280, No. 48, p. 40130-40134.
Haruyama, T., et al., "Epsilon Subunit stops rotation of thermophilic F1-ATPase; Single molecular analysis of the inhibition by the Epsilon subunit.," Biophysics, 2006, vol. 46, Sup2, p. 5222 (1P301).
Appl Microbiol. 1975; 30, 713-721.
J. Am. Soc. Brew. Chem. 1976; 34, 145-150.
Plant Cell Physiol. 1979; 20, 145-155.
J. Mol. Cell. Cardiol. 1986; 18, 517-527.
Nature 1977; 265, 756-758.
Proc. Nat. Acad. Sci. U.S.A. 1979; 76; 5445-5449.
J. Biol. Chem. 1980; 255, 3987-3993.
Nat Biotechnol. 2007; 25 (2):170-172.
J. Biol Chem. 2003; vol. 278, No. 38, p. 36013-36016.
Biophysics. The Biophysical Society of Japan Dai 40 Kai Nenkai Koen Yokoshu; 2002, vol. 42, Sup.2, p. S147(2O1615).
Proc. Nat. Acad. Sci. U.S.A. 2003; vol. 100, No. 16, p. 9314-9318.
J. Biol Chem. 2000; vol. 275, No. 46, p. 35746-35750.
FEBS Lett., 2005, vol. 579, No. 30, p. 6875-6878.
J. Biol Chem. 2005; vol. 280, No. 48, p. 40130-40134.
Biophysics, 2006, vol. 46, Sup2, p. s222 (1P301).

* cited by examiner

Primary Examiner — Scott Long
Assistant Examiner — Arthur S Leonard
(74) Attorney, Agent, or Firm — Joseph H. Kim; JHK Law

(57) ABSTRACT

The object of the present invention is to provide a substance, which is easy to handle and enables the measurement of ATP with a high sensitivity regardless of the concentration of protein, and further a measuring method of ATP using the substance. Such object is solved with a fluorescence labelled fusion protein obtained by attaching two types of fluorescent substances of potential donor and acceptor for fluorescence resonance energy transfer (FRET) respectively to a protein which can cause structural changes depending on ATP binding, namely ε protein, which is the subunit of ATP synthetase, and further solved by contacting the fluorescence labelled fusion protein with a subject substance and then measuring the fluorescence spectra.

3 Claims, 4 Drawing Sheets

FLUORESCENTLY LABELED FUSION PROTEIN FOR ASSAYING ADENOSINE TRIPHOSPHATE

TECHNICAL FIELD

The present invention relates to a fluorescence labelled fusion protein for measuring adenosine triphosphate and a measuring method of adenosine triphosphate using the fluorescence labelled fusion protein as a fluorescent protein probe.

BACKGROUND ART

Adenosine triphosphate (hereinafter simply referred to as "ATP") is the energy currency in living organisms.

Until now, the most commonly used measuring method of ATP has been luciferin-luciferase system and a small amount of ATP in a solution can be measured selectively with this system (Nonpatent Document Nos. 1 to 3). Reagents and kits regarding ATP measurement by luciferin-luciferase system already have been commercially available and commonly used. For example, LL100-1/ATP Luminescence Kit (TOYO INK GROUP), ATPlite ATP detection system (Perkin Elmer) and the like is included. However, in the case where luciferase is expressed in the cells to measure ATP concentration in a living organism, quantitative measurement is difficult and thus following the change in ATP concentration with a high temporal resolution is difficult, because of the drawbacks that luminescence of luciferase is dark and also the amount of luminescence is dependent on the concentration of protein.

Further, since luciferase has an ATP-hydrolytic activity, it can be considered that expressing luciferase in cells may change ATP concentration.

Another method is high performance liquid chromatography (HPLC) method, where ATP is detected by separating it from other substances through the use of an appropriate column (Nonpatent Document No. 4). The method enables quantitative measurement of ATP in solution, but the operation is so complicated that measuring ATP in vivo, namely in living cells, is impossible.

Alternatively, measuring ATP by $^{31}$P-NMR method has also been reported (Nonpatent Document Nos. 5 to 7). In this approach, its merit is that ATP concentration in a living organism can be accurately obtained without forcedly expressing proteins such as luciferase. However, its poor spatial resolution and poor sensitivity limit the measurement only to the tissue level and its poor temporal resolution provides a drawback of requiring long measuring time. Further, extremely expensive measuring equipment is also a major drawback.

In reality, in order to measure ATP in a living organism, there are overwhelmingly many cases where the living organism is broken to obtain extract and the ATP in the extract is measured by luciferase or HPLC. However, in such a case where a living organism is broken to obtain extract and ATP in the extract is measured, there is a drawback that ATP is hydrolyzed before measurement.

As a new measuring method, a measuring method using fluorescence resonance energy transfer (fluorescence resonance energy transfer: FRET) technique has been reported where cyan fluorescent protein (CFP) and yellow fluorescent protein (YFP) are attached to CBS domain of inosine monophosphate dehydrogenase 2 (IMPDH2), which is a protein reactive with adenosine nucleic acids such as ATP, ADP and AMP (Nonpatent Document No. 8).

[Nonpatent Document No. 1] Appl Microbiol. 1975; 30, 713-721.
[Nonpatent Document No. 2] J. Am. Soc. Brew. Chem. 1976; 34, 145-150.
[Nonpatent Document No. 3] Plant Cell Physiol. 1979; 20, 145-155.
[Nonpatent Document No. 4] J. Mol. Cell. Cardiol. 1986; 18, 517-527.
[Nonpatent Document No. 5] Nature 1977; 265, 756-758.
[Nonpatent Document No. 6] Proc. Nat. Acad. Sci. U.S.A. 1979; 76, 7445-7449.
[Nonpatent Document No. 7] J. Biol. Chem. 1980; 225, 3987-3993
[Nonpatent Document No. 8] Nat. Biotechnol. 2007; 25 (2): 170-172.

DISCLOSURE OF THE INVENTION

Problems to be Solved

The subject of the present invention is to provide a substance, which enables the measurement of ATP with easy handling and with a high sensitivity regardless of the concentration of protein. Further, the subject of the present invention is to provide a measuring method of ATP using the substance.

Means to Solve the Problems

The present inventors have strenuously studied to solve the matters described above and as a result, have focused on the presence of a protein which can cause structural changes depending on ATP binding, namely ε protein, which is the subunit of ATP synthetase. Through the use of the properties of the protein, a novel fluorescence labelled fusion protein was prepared by attaching two types of fluorescent substances of potential donor and acceptor for fluorescence resonance energy transfer (hereinafter simply referred to as "FRET"), respectively, to ε protein, thereby having completed the present invention (see FIG. 1).

Therefore, the present invention consists of the following:
1. A fluorescence labelled fusion protein obtained by attaching two types of fluorescent substances of potential donor and acceptor for FRET, respectively, to a protein comprising a part of an amino acid sequence constituting ε protein, which is a subunit of ATP synthetase.
2. The fluorescence labelled fusion protein according to the preceding aspect 1, wherein the part of an amino acid sequence constituting said ε protein comprises a site which can cause structural changes at least specifically to ATP.
3. The fluorescence labelled fusion protein according to the preceding aspect 1 or 2 obtained by attaching the two types of fluorescent substances of potential donor and acceptor, respectively, to N- and C-terminal domains of the protein comprising a part of an amino acid sequence constituting said ε protein.
4. The fluorescence labelled fusion protein according to any one of the preceding aspects 1 to 3, wherein the protein comprising a part of an amino acid sequence constituting said ε protein includes 1 to 8 amino acid substitutions, deletions, insertions or additions relative to an amino acid sequence constituting wild type ε protein.
5. The fluorescence labelled fusion protein according to any one of the preceding aspects 1 to 4, wherein the fluorescent label is a fluorescent protein and a combination of donor and acceptor is any combination of cyan fluorescent protein (CFP) and yellow fluorescent protein (YFP), blue fluorescent protein (BFP) and green fluorescent protein (GFP), or green fluorescent protein (GFP) and red fluorescent protein (RFP).

6. A DNA encoding the fluorescence labelled fusion protein according to any one of the preceding aspects 1 to 5.

7. A vector comprising the DNA according to the preceding aspect 6 and capable of expressing a fluorescence labelled fusion protein from the DNA.

8. A measuring method of ATP comprising at least the following steps:

1) contacting the fluorescence labelled fusion protein according to any one of the preceding aspects 1 to 5 with a subject substance to cause a reaction;

2) reacting the fluorescent protein described above with the subject substance and then measuring fluorescence emitted from a mixture of the fluorescence labelled fusion protein and the subject substance.

9. The measuring method according to the preceding aspect 8, wherein the subject substance is a living organism containing ATP and ATP is brought into contact with the fluorescence labelled fusion protein to cause a reaction in the living organism.

10. The measuring method according to the preceding aspect 9, wherein a method of contacting ATP with fluorescence labelled fusion protein to cause a reaction in the living organism is performed by introducing the DNA according to the preceding aspect 6 into the living organism and expressing the fluorescence labelled fusion protein in the living organism.

11. An ATP-measuring reagent comprising the fluorescence labelled fusion protein according to any one of the preceding aspects 1 to 4, the DNA according to the preceding aspect 6 or the plasmid according to the preceding aspect 7.

12. An ATP-measuring reagent kit comprising the DNA according to the preceding aspect 6 or the vector according to the preceding aspect 7, and a reagent necessary for expressing a fluorescence labelled fusion protein.

Effects of Invention

ATP is the cell's energy currency and to know the amount of ATP in living cells is medically and biologically important. However, until now, since there have been no practical techniques for the measurement, it has been almost unknown whether ATP concentration in living cells is constantly maintained or dynamically fluctuated, or whether ATP concentration differs from one cell to the next.

ATP concentration can be measured with the ratio of donor to acceptor fluorescence by FRET technique through the use of the fluorescence labelled fusion protein of the present invention as a fluorescent protein probe. The method has major advantage that quantitative capability is not affected by the amount of protein, unlike in the case of using luciferase. ATP in living cells can be easily measured just by genetically introducing the fluorescence labelled fusion protein of the present invention into cells. ATP in organelle can also be measured just by attaching an appropriate organelle transfer signal to the fluorescence labelled fusion protein of the present invention.

The measuring method of ATP of the present invention using the fluorescence labelled fusion protein of the present invention can be conducted by a commonly used fluorescent spectrophotometer or fluorescence microscope, and special devices are not required. Further, its spatial and temporal resolutions for the measurement are equivalent or more than those of conventional methods.

Figure 1:
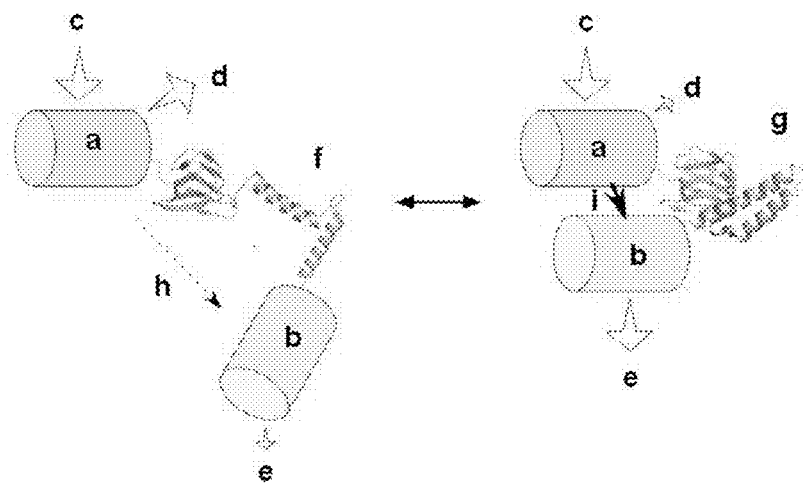
FIG. 1 shows the schematic representation of the fluorescence labelled fusion protein of the present invention. Further, it shows the reaction mode of structural change caused by the reaction of the fluorescence labelled fusion protein with the ATP.

EXPLANATION OF SYMBOLS a CFP
b YFP
c 436 nm
d 475 nm
e 527 nm
f ε protein (non-ATP binding type)
g ε protein (ATP-binding type)
h Low FRET
i High FRET
A Marker
B Total fraction of bacterial body
C Soluble Fraction
D Purified sample

DESCRIPTION OF THE PREFERRED EMBODIMENT

ATP synthetases are classified into F-types and V-types, and F-types are further classified into $F_1$ site and $F_0$ site. $F_1$ site is composed of subunits such as α, β, γ, δ and ε. ε, which is the subunit of ATP synthetase, (hereinafter simply referred to as "ε protein") has a high affinity for ATP, but an extremely low affinity for nucleotides except for ATP such as ADP, dATP and GTP, and further causes structural changes by binding to ATP. Thus, the idea of using its property for measuring ATP has been conceived.

ε protein used in the present invention may be derived from any biological species, but in consideration of the ease of handling, those derived from microorganisms, for example, from *Bacillus* sp. PS3 (GenBank accession No. AB044942 (SEQ. ID. NO: 1)) and *Bacillus subtilis* (GenBank accession No. Z28592 (SEQ. ID. NO: 2)) can preferably be used. Further, ε protein obtained from a bacterial strain other than these bacterial strains can also be used. ε proteins derived from different biological species have different affinities to ATP (J. Biological Chemistry 2003; 278, 36013-36016, FEBS Letters 2005; 579, 6875-6878). Therefore, it is considered that the ATP-measuring reagent sensitive to various concentration ranges can be created by using different ε proteins accordingly from those responding to low concentration ATP to those responding to high concentration ATP like intracellular ATP.

ε protein contains two domains, N- and C-terminal domains. N-terminal domain is composed of amino acids from N-terminal to approximately the 85th of the ε protein, consisting of as much as 10 β-strands. C-terminal domain is composed of amino acids from C-terminal to approximately the 45th of ε protein, consisting of two α helices. C-terminal domain has a folded crystal structure when ε protein is present alone, and it has a stretched structure when the ε protein constitutes a complex with γ protein which is another subunit of ATP synthetase. Further, from the results of biochemical experiments, it is shown that C-terminal domain of ε protein causes structural changes within a complex with γ protein and the like depending on the presence or absence of ATP, thereby having a stretched state in the absence of ATP and folded structure in the presence of ATP. From these facts, it is considered that the C-terminal domain of ε protein is a stretched or a mobile state in the absence of ATP, but a folded compact state on binding to ATP.

In the present invention, "a part of an amino acid sequence constituting ε protein" may be any as long as it is apart of an amino acid sequence constituting a site which can cause structural changes at least specifically to ATP in ε protein, but is not limited in particular. For example, the part may have a construction comprising the two domains of N- and C-terminal domains described above as well as a construction in which these two domains can cause structural changes in the presence of ATP. "A protein comprising a part of an amino acid sequence constituting ε protein" may be whole naturally occurring ε protein or may be one including 1 to 8 amino acid substitutions, deletions, insertions or additions relative to the naturally occurring ε protein as long as it comprises the amino acid sequence constituting a site which can cause structural changes specifically to ATP described above. For example, in order to prevent a substance, which may inhibit the structural changes of ε protein caused by the reaction between the ε protein and ATP, from binding to ε protein, a part of the amino acid sequence may be substituted. Specifically, in an ε protein part, hydrophobic amino acid residue parts (Val9/Val42/Phe67/Leu78: SEQ. ID. NO: 1 and Val9/Val42/Phe67/Leu78: SEQ. ID. NO: 2) necessary for interaction with γ protein, which are the other subunits, can be substituted by hydrophilic amino acid residues.

The fluorescence labelled fusion protein of the present invention is a fusion protein of two types of fluorescent substances and a protein comprising a part of an amino acid sequence constituting ε protein.

Two types of fluorescent substances to be attached may be those which consist of the combination of potential donor and acceptor for FRET, but are not limited in particular. Herein, FRET is a state where two types of fluorescent substances, which are referred to as donor and acceptor, come closer within a certain distance from each other, light energy absorbed by the donor is transferred to the acceptor. FRET detection is usually carried out by irradiating an excitation wavelength light of donor and measuring the fluorescence intensity of donor or acceptor. In the measurement of fluorescence intensity of donor, when two types of fluorescent substances are in proximity with each other, the fluorescence intensity of the donor becomes lower because the acceptor absorbs the light, while the fluorescence intensity becomes higher by being apart from each other. When the fluorescence intensity of the acceptor is measured, it's vice versa, that is to say, the shorter the distance, the higher the fluorescence intensity and the longer the distance, the lower the intensity.

When the fluorescence labelled fusion protein of the present invention is incorporated in a living organism or expressed in vivo to measure fluorescence, a fluorescent substance useful for potential labeling is also preferred to be a fluorescent protein. A commonly used fluorescent protein can be used. In particular, green fluorescent protein (GFP) represented by the one derived from *Aequorea victoria*, yellow fluorescent protein (YFP) and cyan fluorescent protein (CFP), which are made by introducing various mutation into GFP to change the fluorescence colors, or red fluorescent protein (RFP) represented by the one derived from coral etc. is included. In order that the fluorescent protein exerts FRET function, for example, CFP and YFP, BFP and GFP, or GFP and RFP can be used as the combination of donor and acceptor. These fluorescent proteins can be used from among commercially available fluorescent proteins. For example, the following are useful: CFPs include CFP from Invitrogen, YFPs include YFP from Invitrogen and Phi-Yellow from Evrogen, GFPs include EGFP from Clontech and Tag-GFP from Evrogen, RFPs include DsRed2-monomer from Clontech and HcRed-Tandem from Evrogen.

A fluorescent substance constituting the fluorescence labelled fusion protein of the present invention may be a low molecular-weight fluorescent substance unless it is not reacted with a fluorescence labelled fusion protein in vivo. Examples of the combination of FRET donor/acceptor preferable as a combination of low-molecular weight fluorescent substances include the following: pyrene maleimide/fluorescein maleimide, CPM/fluorescein maleimide, fluorescein maleimide/Texas red maleimide, Alexa 488 maleimide/Texas red maleimide, tetramethylrhodamine maleimide/Alexa 633 maleimide and Cy3/Cy5.

Fluorescent substances constituting the fluorescence labelled fusion proteins of the present invention can be attached to N- and C-terminal domains of a protein comprising a part of an amino acid sequence constituting ε protein. More specifically, if fluorescent substances are low-molecular weight fluorescent substances, they can be attached to appropriate sites of N- and C-terminal domains. If fluorescent substances are fluorescent proteins, not only they can be attached to C- and N-terminals, but also they can be inserted into any loop region shown by the positions 19-21, 34-40, 54-57 and 71-74 in amino acid sequence represented by SEQ. ID. NO: 1 in the N-terminal side.

The fluorescence labelled fusion protein of the present invention can be prepared using a well known method per se. For example, it can be prepared by a genetic engineering technique. The method for fluorescently labeling with a low molecular weight fluorescence can also employ a well known method per se.

Regarding the present invention, besides the fluorescence labelled fusion protein described above, the present invention covers DNA encoding the fluorescence labelled fusion protein. Here, DNA encoding the fluorescence labelled fusion protein means DNA having a base sequence capable of expressing the fluorescence labelled fusion protein explained above. In particular, for example, a base sequence encoding an amino acid sequence obtained by attaching each fluorescent protein to an amino acid sequence itself constituting protein consisting of amino acid sequences represented by SEQ. ID. NO: 1 or SEQ. ID. NO: 2 (referred to herein as "naturally occurring protein"), or an amino acid sequence including 1 to 8 amino acid substitutions, deletions, insertions or additions relative to the amino acid sequence described above is included. More specifically, DNA or the like encoding an amino acid sequence consisting of the one obtained by adding amino acids constituting each fluorescent protein to an amino acid constituting ε protein consisting of sequences represented by SEQ. ID. NO: 1 and SEQ. ID. NO: 2, or an amino acid sequence including 1 to 8 above described amino acid substitutions, deletions, insertions or additions relative to those sequences is included. Further, DNAs of the present invention includes any DNAs encoding proteins having the same amino acid sequences as fluorescence labelled fusion proteins due to the degeneracy of genetic codon and also complementary strands thereof, in addition to DNAs consisting of base sequences derived from *Bacillus* sp. PS3 (GenBank accession No. AB044942) and derived from *Bacillus subtilis* (GenBank accession No. Z28592).

The vector of the present invention is one capable of expressing the fluorescence labelled fusion protein and comprising the DNA encoding the fluorescence labelled fusion protein of the present invention. For example, fluorescent protein DNAs of potential donor and acceptor for FRET are fused to DNA encoding the whole or part of protein. The vector can be prepared by, for example, introducing them into cloning sites of an expression vector well known per se.

In the following, the measuring method of ATP by using the fluorescence labelled fusion protein of the present invention for measuring will be explained. A subject substance may be a solution containing ATP, and the measurement can be performed by contacting the subject substance with the fluorescence labelled fusion protein prepared above as a fluorescent protein probe for a certain period of reaction. The solution containing ATP can be obtained from cell extract and the like, for example.

Measurement conditions are as follows:

Subject substances may be any as long as they contains ATP and, for example, a solution containing ATP, biological samples such as cells, and ATP extracts from biological samples are included. The concentration of fluorescent protein probe can be determined as appropriate and selected from a range between 10 and 10000 nM, for example. Lysis buffer can be any and is not limited in particular and, for example, lysis buffers having pH which allows fluorescence to emit from a fluorescent substance at an optimal condition can be selected. In particular, when YFP is used as a fluorescent substance, a buffer at pH 7 or higher is preferably used because the fluorescence of YFP decreases in acidic side. The reaction temperature may be any as long as a fluorescent protein probe can cause structural changes and, for example, $37\pm1°$ C. or $25\pm1°$ C. can be used for measurement. The reaction time can also be determined as appropriate, preferably one minute or more, but is within the period allowing protein to retain its activity. Additives can be added to the reaction as appropriate. For example, 0.05% surfactant (TritonX100) or 1 mg/mL bovine serum albumin (BSA) can be added for stabilization. Chelating agents such as EDTA and EGTA, for example, may be added to avoid the effects of magnesium present in the subject sample.

The fluorescence spectra of the subject substance after the reaction terminated can be measured through the use of a fluorometer by irradiating the substance with excitation light of the donor, measuring each fluorescence intensity in the wavelength in which peaks of single fluorescence intensity of each fluorescent substance are provided, and calculating the ratio. On the other hand, ATP solution at a known concentration is prepared, the ratio of fluorescence intensities are obtained likewise and the calibration curve is made. The ATP concentration of the specimen can be obtained by using this calibration curve.

Intracellular ATP can be measured by introducing a vector capable of expressing the fluorescence labelled fusion protein into a living organism, for example, into cells being the subject substance, by such approaches as DNA introduction method, incubating the cells for a defined period and expressing the fluorescence labelled fusion protein, or introducing fluorescence labelled fusion protein itself by microinjection and allowing ATP in a living organism to react with the fluorescence labelled fusion protein. ATP in a particular organelle can be measured by attaching a transfer signal of the organelle of interest to a fluorescence labelled fusion protein by a well known method per se. For example, a base sequence encoding the signal of interest may be introduced into a vector capable of expressing the fluorescence labelled fusion protein. The measurement can be performed by directly observing cells in which the fluorescence labelled fusion protein was expressed, under a fluorescence microscope. Further, the amount of fluorescence of donor and acceptor can be measured by a flow cytometer.

The present invention covers a reagent comprising a fluorescence labelled fusion protein or a vector capable of expressing the fluorescence labelled fusion protein. Further, it also covers an ATP-measuring reagent kit comprising a vector capable of expressing a fluorescence labelled fusion protein and a reagent necessary for expressing the fluorescence labelled fusion protein.

EXAMPLE

In order to help understanding of the invention, the present invention will be explained with reference to specific Examples below, but needless to say, the present invention is not limited to these Examples.

Example 1

Preparation of Fluorescence Labelled Fusion Protein

1) ε Protein
   a. ε protein derived from *Bacillus* sp. PS3 (SEQ. ID. NO: 1)
   b. ε protein derived from *Bacillus subtilis* (SEQ. ID. NO: 2)

Each ε protein described above was obtained in the same way as that in described in J. Biological Chemistry 2003; 278, 36013-36016. Alanine and asparagine were attached to the C-terminal of the amino acid sequence derived from *Bacillus subtilis* represented by SEQ. ID. NO: 2 described above. Further, in a protein consisting of the amino acid sequence represented by SEQ. ID. NO: 1 derived from *Bacillus* sp. PS3 described above, hydrophobic amino acid residue parts (Val9/Val42/Phe67/Leu78: SEQ. ID. NO: 1) necessary for interaction with γ protein, which are the other subunits, were substituted by hydrophilic amino acid residues. The altered proteins obtained from a and b described above were termed as A and B, respectively.

2) Preparation of Fluorescence labelled Fusion Protein cDNA encoding CFP was attached to the 5' terminal of cDNA encoding each altered protein A or B described above and cDNA encoding YFP was attached to the 3' terminal, and then fused.

DNA encoding ε protein was amplified by PCR method and the terminal portion was cleaved with restriction enzymes ClaI and EcoRI. DNA encoding CFP was amplified by PCR method likewise and the terminal portion was cleaved with restriction enzymes NdeI and ClaI. CFP-ε fusion plasmid was prepared by binding the two fragments to each other (by binding between ClaI ends) and then ligating it into NdeI and EcoRI sites of pET23a vector. Subsequently, DNA encoding YFP was amplified by PCR method and then the terminal portion was cleaved with EcoRI and SalI. During PCR, histidine-tag was fused to the C-terminal of YFP. An expression plasmid of CFP-ε-YFP fusion protein was prepared by ligating it into the EcoRI and SalI sites of the forementioned CFP-ε fusion plasmid.

*E. coli* BL21 (DE3) strain into which the prepared plasmid was introduced was incubated, and IPTG was added into a medium to induce the expression of protein. The incubated *E. coli* were harvested, homogenized with ultrasonic, and then centrifuged to obtain supernatant, which was then purified by Ni-chelating column and anion exchange column chromatography.

3) Confirmation of the Prepared Fluorescence Labelled Fusion Protein

Figure 2:
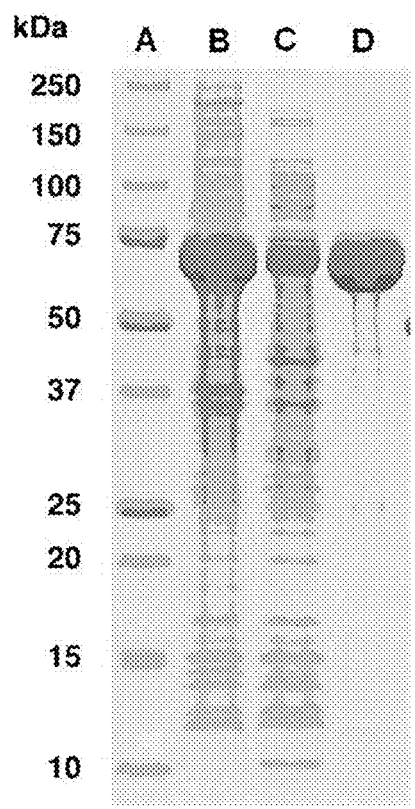
FIG. 2 shows the confirmation results of SDS-PAGE of the fluorescence labelled fusion protein prepared (Example 1).

A band was confirmed at the position of the predicted molecular weight by SDS electrophoresis (see FIG. 2). Further, the absorption spectra of the purified fusion protein were measured to confirm the existence of both CFP and YFP absorptions.

Fluorescence labelled fusion protein created by fusing each fluorescent protein to altered proteins A and B described in 1) above were termed as fluorescence labelled probes A and B.

Test Example 1

Measurement Using Fluorescence Labelled Probe A

1. Fluorescence labelled probe A was diluted in a buffer containing the following stabilizer so as to become a final concentration of approximately 100 nM to prepare a fluorescent probe solution. 0.05% surfactant (TritonX100) or 0.1% BSA was added to the buffer (50 mM MOPS-KOH (pH7.5), 50 mM KCl, 2 mM $MgCl_2$) in order to stabilize the probe.
2. The fluorescent probe solution was diluted with the mixed buffer so as to adjust the ATP concentration to be 0 to 1 mM. A purified ATP dissolved in water and neutralized was used. ATP concentration was calculated by using the molar extinction coefficient ($15.4 \times 10^3$) at 254 nm of ATP. After the reaction for 1 minute at 37° C., fluorescence was excited at 435 nm by using spectrophotometer (JASCO FP-6500), and the ratio of fluorescence intensities at 527 nm and 475 nm at which reaction with ATP occurred was plotted.

Figure 3:
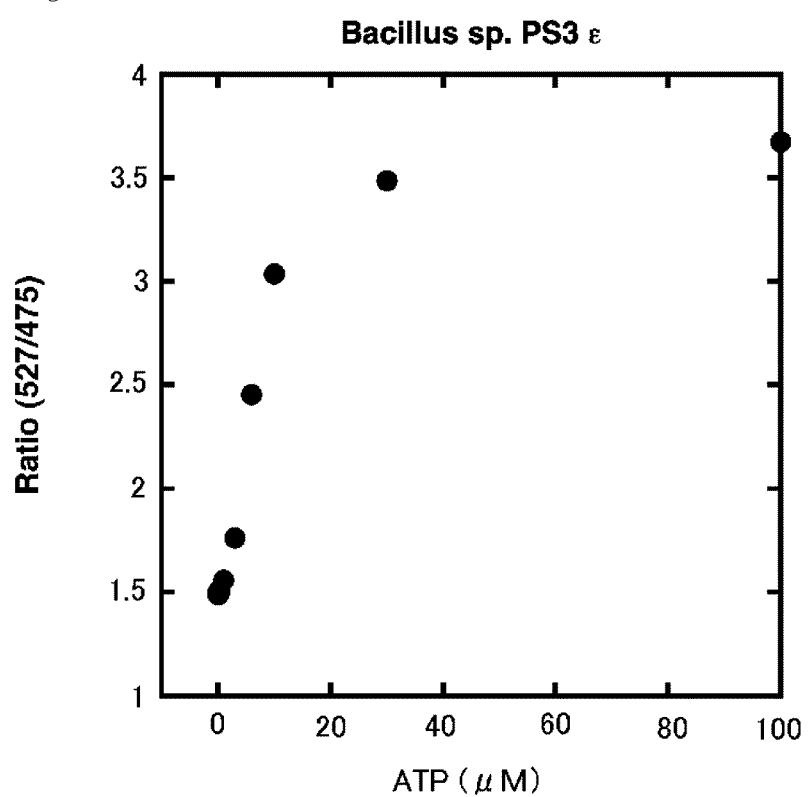
FIG. 3 shows the results measured by using fluorescence labelled probe A (derived from *Bacillus* sp. PS3) (Test Example 1).

The measurement result described above was shown in FIG. 3. A significant change in fluorescence spectrum was observed at a concentration of around 10 μM.

Test Example 2

Measurement Using Fluorescence Labelled Probe B

The concentration of fluorescence labelled probe B was adjusted to be approximately 100 nM, and ATP was added so as to become a final concentration of 0 to 6 mM. Measurement was conducted by the same method as that of Test Example 1.

Figure 4:
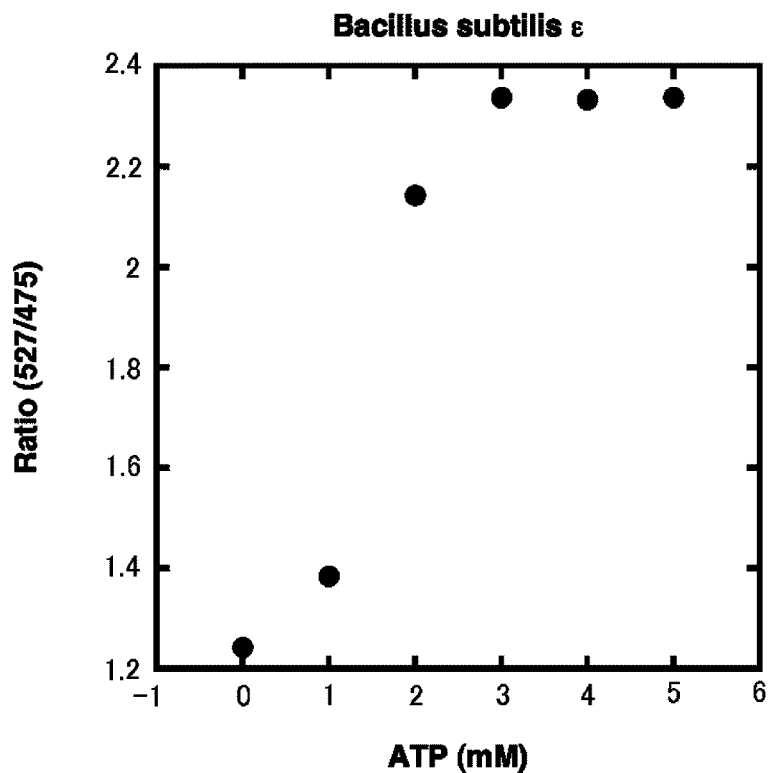
FIG. 4 shows the results measured by using fluorescence labelled probe B (derived from *Bacillus subtilis*) (Test Example 2).

The measurement result described above was shown in FIG. 4. A significant change of fluorescence spectrum was observed at a concentration of around 1.5 mM.

Example 2

Preparation of In Vivo Expression Plasmid of Fluorescence Labelled Fusion Protein 1) ε Protein Alanine and asparagine were attached to the C-terminal side of the amino acid sequence of ε protein b (ε protein derived from *Bacillus subtilis*: SEQ. ID. NO: 2) described in Example 1. Further, hydrophobic amino acid residue parts necessary for interaction with γ protein, which are the other subunits, were substituted by hydrophilic amino acid residues (V9T/V42K/F67T/L78N: SEQ. ID. NO: 2). The altered protein obtained like this was termed as B1.

2) Preparation of In Vivo Expression Plasmid of Fluorescence Labelled Fusion Protein cDNA encoding CFP was attached to the 5' terminal of cDNA encoding altered protein B1 and cDNA encoding YFP was attached to the 3' terminal.

DNA encoding ε protein was amplified by PCR method and then the terminal portion was cleaved with restriction enzyme ClaI and EcoRI. DNA encoding CFP was amplified by PCR method likewise and then the terminal portion was cleaved with restriction enzymes XhoI and ClaI. CFP-ε fusion plasmid was prepared by binding the two fragments to each other (by binding between ClaI ends) and then ligating it into XhoI and EcoRI sites of pcDNA3.1 vector. Subsequently, DNA encoding YFP was amplified by PCR method and then the terminal portion was cleaved with EcoRI and HindIII. An expression plasmid of CFP-ε-YFP fusion protein (CFP-ε-YFP fusion plasmid) was prepared by ligating it into EcoRI and HindIII sites of the forementioned CFP-εfusion plasmid. Then, 2xCoxVIII signal (SEQ. ID. NO: 3: amino acid sequence) and 3xSV40 Large T antigen signal (SEQ. ID. NO: 4: amino acid sequence) were ligated respectively to the upstream of CFP in CFP-ε-YFP fusion plasmid by using an ordinary method to prepare 2xCoxVIII signal-CFP-ε-YFP fusion plasmid and 3xSV40 Large T antigen signal-CFP-ε-YFP fusion plasmid. 2xCoxVIII signal was a mitochondrial transport signal and 3xSV40 Large T antigen signal was nuclear transport signal.

Test Example 3

Expression of Fluorescence Labelled Probe in Mammalian Cell

Three types of plasmids (2xCoxVIII signal-CFP-ε-YFP fusion plasmid, 3xSV40 Large T antigen signal-CFP-ε-YFP fusion plasmid, CFP-ε-YFP fusion plasmid) prepared in Example 2 were introduced into HeLa cells by lipofection method, respectively. Then, HeLa cells were incubated in medium by using a glass bottom dish and the probes were expressed.

The glass bottom dish was placed on a fluorescence microscope, irradiated with excitation light at 427 nm and images were obtained with a highly sensitive cooled CCD camera.

Figure 5:
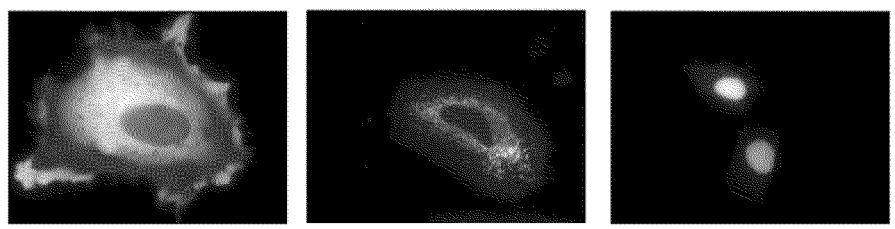
FIG. 5 shows photographs of the results after fluorescence labelled probes were expressed in mammalian cells (Test Example 3).

The results are shown in FIG. 5. Photographs from the left to the right are cytoplasm, mitochondria and nucleus in which fluorescence labelled probes were expressed. It was found that the fluorescence labelled probe of the present invention can be expressed in any place in a cell.

Test Example 4

Follow-Up of ATP Concentration Changes in a Single Cell

The plasmid (CFP-ε fusion plasmid-YFP) not containing a signal sequence prepared in Example 2 was introduced into HeLa cells by lipofection method. Then, HeLa cells were incubated in culture medium in a glass bottom dish to express the probe.

Fluorescent images were taken at each time point of 12, 14, 16, 18, 20, 22, 24 and 26 minutes after initiating the imaging experiment. At each time point, the glass bottom dish was place on the microscope and irradiated with excitation light at 427 nm. CFP images (image after passing through a 483 nm bandpass filter) and YFP images (image after passing through a 542 nm bandpass filter) were alternately taken by switching between 483 nm- and 542 nm-bandpass filters through the use of a filter changer. In order to take images, a highly sensitive cooled CCD camera was used. Meanwhile, sodium azide and 2 deoxyglucose, which are inhibitors of ATP synthesis, were added at the stage of 15 minutes after initiating the imaging experiment.

Figure 6:
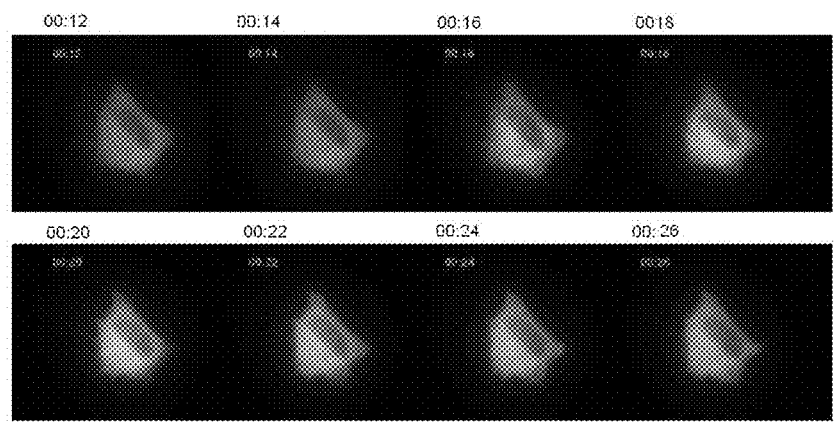
FIG. 6 shows photographs representing time course in intracellular ATP concentration by using the fluorescence labelled probes (Test Example 4).

The results were shown in FIG. 6. The ratios of YFP images to CFP images were analyzed from false color images. Photographs from top left were taken at 12, 14, 16, 18, 20, 22, 24, 26 minutes after the initiation of imaging. Red shows a state of high YFP/CFP ratio (meaning high ATP concentration) (12 and 14 min.) and blue shows a state of low YFP/CFP ratio (low ATP concentration) (22, 24 and 26 min.). Immediately after 15 minutes at which an inhibitor of ATP synthesis was added, the decreasing intracellular ATP concentration can be seen.

INDUSTRIAL APPLICABILITY

As described in detail above, it was demonstrated that by using the fluorescence labelled fusion protein of the present invention, even if ATP concentration is low, it can be measured with a good sensitivity. Further, it was confirmed that sensitivities to ATP are different when using proteins derived from *Bacillus* sp. PS3 and *Bacillus subtilis*. It was considered that these differences in sensitivities are caused by each protein having a different specificity, when being measured at the same temperature condition because each bacterial strain has a different optimum temperature for growth.

Further, it was shown that ATP in a living organism can be measured with a good sensitivity by using DNA encoding the fluorescence labelled fusion protein to express it in vivo. It is believed that ATP concentration in a living organism can be measured by introducing a fluorescence labelled fusion protein directly into cells. Thereby, the fluorescence labelled fusion protein of the present invention can be provided as a protein reagent for easily measuring ATP in the field of biological research or a DNA reagent for measuring intracellular ATP.

ATP acts as a neurotransmitter and it has been recently reported that the reduction in intracellular ATP concentration is associated with the initiation of apoptosis. The fluorescence labelled fusion protein of the present invention is expected to be used not only in basic researches but also in drug development since ATP is involved in the phenomena targeting such pharmaceuticals.

For example, it is expected that the fluorescence labelled fusion protein of the present invention can be used as screening of anticancer agents, diagnosing of diabetes, and drug development.

Differences in efficacies of anticancer agents big largely depend on cancer types and patients. Therefore, a method for examining the best combination of anticancer agents is often adopted by measuring the amounts of ATP in cell extracts through the use of luciferase, after incubating cancer cells from a patient and applying to the combination of many anticancer agents (Methods Mol Med 2005 vol. 110 p 101-120). It is expected that making use of the fluorescence labelled fusion protein of the present invention for measuring the amount of ATP in cancer cells enables examining of the effects of anticancer agents more rapidly and more quantitatively.

Diabetes is caused by the suppression of insulin secretion from insulin-secreting cells in pancreatic islet. It is considered that the increase in ATP concentration in insulin-secreting cells accompanied by the increase in blood glucose level is an important step in the insulin secretion (Diabetes, 53 Suppl 3, p 176-80, 2004). Diabetes is considered to have an extremely complicated pathogenic mechanism, and thus identifying the cause is difficult. The present invention allows examining whether ATP concentration in islet cells depends on blood glucose level, which can be a technique to identify the cause of disease. Further, it is considered to be useful for developing diabetic drugs by using ATP concentration as an indicator.

The invention claimed is:

1. A method of measuring ATP comprising at least the following steps:
   1) contacting a subject substance to a fluorescently labelled fusion protein obtained by individually attaching to an ε protein subunit of adenosine triphosphate (ATP) synthetase two types of fluorescent substances that act as a potential donor and acceptor for a fluorescence resonance energy transfer (FRET) reaction;
   2) measuring fluorescence emitted from the reaction of the fluorescently labeled fusion protein and the subject substance,
   wherein said ε protein is selected from one of the following (a) and (b):
   (a) a protein having an amino acid sequence including 1 to 8 substitutions in SEQ. ID. NO: 1; and
   (b) a protein having an amino acid sequence including 1 to 8 substitutions in SEQ. ID. NO: 2,
   wherein said ε protein in (a) or (b) has one or more hydrophobic amino acid residues substituted with hydrophilic amino acid residues, wherein the hydrophobic residue is selected from the group consisting of Val9, Val42, Phe67, and Leu 78 in SEQ ID NO:1 or SEQ ID NO: 2.

2. The method according to claim 1, wherein said contacting occurs within a cell containing ATP.

3. The method according to claim 2, wherein said contacting within a cell is performed by introducing DNA encoding the fluorescently labelled fusion protein.

* * * * *

SEQUENCE LISTING

```
<160> NUMBER OF SEQ ID NOS: 4

<210> SEQ ID NO 1
<211> LENGTH: 133
<212> TYPE: PRT
<213> ORGANISM: Artificial Sequence
<220> FEATURE:
<223> OTHER INFORMATION: Bacillus sp.

<400> SEQUENCE: 1

Met Lys Thr Ile His Val Ser Val Val Thr Pro Asp Gly Pro Val Tyr
1               5                   10                  15

Glu Asp Asp Val Glu Met Val Ser Val Lys Ala Lys Ser Gly Glu Leu
            20                  25                  30

Gly Ile Leu Pro Gly His Ile Pro Leu Val Ala Pro Leu Glu Ile Ser
        35                  40                  45

Ala Ala Arg Leu Lys Lys Gly Gly Lys Thr Gln Tyr Ile Ala Val Ser
    50                  55                  60

Gly Gly Phe Leu Glu Val Arg Pro Asp Lys Val Thr Ile Leu Ala Gln
65                  70                  75                  80

Ala Ala Glu Arg Ala Glu Asp Ile Asp Val Leu Arg Ala Lys Ala Ala
                85                  90                  95

Lys Glu Arg Ala Glu Arg Arg Leu Gln Ser Gln Gln Asp Asp Ile Asp
```

```
                    100                 105                 110
Phe Lys Arg Ala Glu Leu Ala Leu Lys Arg Ala Met Asn Arg Leu Ser
            115                 120                 125

Val Ala Glu Met Lys
        130

<210> SEQ ID NO 2
<211> LENGTH: 132
<212> TYPE: PRT
<213> ORGANISM: Artificial Sequence
<220> FEATURE:
<223> OTHER INFORMATION: Bacillus subtilis

<400> SEQUENCE: 2

Met Lys Thr Val Lys Val Asn Ile Val Thr Pro Asp Gly Pro Val Tyr
1               5                   10                  15

Asp Ala Asp Ile Glu Met Val Ser Val Arg Ala Glu Ser Gly Asp Leu
            20                  25                  30

Gly Ile Leu Pro Gly His Ile Pro Thr Val Ala Pro Leu Lys Ile Gly
        35                  40                  45

Ala Val Arg Leu Lys Lys Asp Gly Gln Thr Glu Met Val Ala Val Ser
    50                  55                  60

Gly Gly Phe Val Glu Val Arg Pro Asp His Val Thr Ile Leu Ala Gln
65                  70                  75                  80

Ala Ala Glu Thr Ala Glu Gly Ile Asp Lys Glu Arg Ala Glu Ala Ala
                85                  90                  95

Arg Gln Arg Ala Gln Glu Arg Leu Asn Ser Gln Ser Asp Asp Thr Asp
            100                 105                 110

Ile Arg Arg Ala Glu Leu Ala Leu Gln Arg Ala Leu Asn Arg Leu Asp
        115                 120                 125

Val Ala Gly Lys
    130

<210> SEQ ID NO 3
<211> LENGTH: 71
<212> TYPE: PRT
<213> ORGANISM: Artificial Sequence
<220> FEATURE:
<223> OTHER INFORMATION: 2xCoxVIII signal peptide

<400> SEQUENCE: 3

Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu Gly Asp Pro
            20                  25                  30

Met Ser Val Leu Thr Pro Leu Leu Leu Arg Gly Leu Thr Gly Ser Ala
        35                  40                  45

Arg Arg Leu Pro Val Pro Arg Ala Lys Ile His Ser Leu Gly Asp Pro
    50                  55                  60

Lys Asp Pro Pro Val Ala Thr
65                  70

<210> SEQ ID NO 4
<211> LENGTH: 66
<212> TYPE: PRT
<213> ORGANISM: Artificial Sequence
<220> FEATURE:
<223> OTHER INFORMATION: 3xSV40 Large T antigen signal peptide

<400> SEQUENCE: 4
```

```
Met Ala Asp Pro Lys Lys Arg Lys Val Asp Pro Lys Lys Lys Arg
1               5               10              15

Lys Val Asp Pro Lys Lys Lys Arg Lys Val Ser Gly Arg Met Arg Gly
                20              25              30

Ser His His His His His His Gly Met Ala Ser Met Thr Gly Gly Gln
        35                  40              45

Gln Met Gly Arg Asp Leu Tyr Asp Asp Asp Asp Lys Asp Pro Pro Val
    50              55                  60

Ala Thr
65
```